(12) United States Patent
Bell

(10) Patent No.: US 7,306,461 B2
(45) Date of Patent: Dec. 11, 2007

(54) CARRIER AND SEATING INSTRUMENT FOR DENTAL DEVICES

(75) Inventor: A. Milton Bell, Cliffside Park, NJ (US)

(73) Assignee: New York University, New York, NY (US)

( * ) Notice: Subject to any disclaimer, the term of this patent is extended or adjusted under 35 U.S.C. 154(b) by 641 days.

(21) Appl. No.: 10/361,899

(22) Filed: Feb. 6, 2003

(65) Prior Publication Data

US 2004/0157189 A1    Aug. 12, 2004

(51) Int. Cl.
*A61C 3/14* (2006.01)
(52) U.S. Cl. .................................................... 433/159
(58) Field of Classification Search ................ 433/159, 433/160, 4; 606/205–208, 210–211
See application file for complete search history.

(56) References Cited

U.S. PATENT DOCUMENTS

| | | | | |
|---|---|---|---|---|
| 1,300,495 | A * | 4/1919 | Shank | 81/424.5 |
| 3,530,584 | A * | 9/1970 | Karlstrom | 433/225 |
| 3,898,738 | A * | 8/1975 | Linder | 433/159 |
| 4,189,839 | A * | 2/1980 | Manuel | 433/4 |
| 5,120,221 | A * | 6/1992 | Orenstein et al. | 433/159 |
| 5,507,643 | A * | 4/1996 | Klein | 433/141 |
| 5,525,059 | A * | 6/1996 | Lee | 433/141 |
| 5,562,447 | A * | 10/1996 | Moy et al. | 433/150 |
| 6,193,514 | B1 * | 2/2001 | Horan | 433/141 |
| 6,241,523 | B1 * | 6/2001 | Nardi | 433/172 |
| 6,699,039 | B2 * | 3/2004 | Dryer | 433/159 |

* cited by examiner

*Primary Examiner*—John J Wilson
(74) *Attorney, Agent, or Firm*—Fay Kaplun & Marcin, LLP

(57) ABSTRACT

Apparatus for manipulating a dental device comprises first and second gripping elements rotatably coupled to one another for movement between a gripping configuration in which a first gripping surface of the first gripping element is positioned adjacent a second gripping surface of the second gripping element to grip a dental device there between and a release configuration in which the first and second gripping surfaces are spaced from one another, wherein each of the first and second gripping surfaces includes a device receiving recess shaped to accommodate a gripping portion of a device to be gripped by the apparatus and a locking mechanism for locking the first and second gripping elements in the gripping configuration. The apparatus may further include a seating surface for applying a seating force to a bearing surface of the dental device.

19 Claims, 3 Drawing Sheets

CARRIER AND SEATING INSTRUMENT FOR DENTAL DEVICES

FIELD OF THE INVENTION

The present invention is applicable to the field of devices used in dentistry.

BACKGROUND INFORMATION

Many branches of dentistry require the use of various small devices for restoring a tooth to normal form and function. For example in the field of operative dentistry, the restoration of teeth often requires the insertion of posts, screws and/or pins into a tooth to provide support and/or retention of the restorative material. Often the teeth being treated are non-vital—i.e., the nerve of the tooth has been removed from the root canal. These teeth are often structurally weak and may require strengthening to withstand the forces applied by the jaw. An endontically treated tooth is frequently treated by the insertion of a prefabricated post that is cemented into the root canal while providing for retention of a core. The core provides a base upon which the final crown will be placed to restore the clinical crown of the tooth. In this type of procedure, pins, screws and other small dental devices are inserted into the tooth to act as fasteners and as strengthening elements.

However, serious harm to the patient is possible if such a device is accidentally dropped into the patient's mouth. Swallowing such a device may cause injury to the patient, and in any case greatly complicates the procedure. Due to this potential for injury, extra care is required in performing such procedures which are consequently more time consuming and which require increased skill.

SUMMARY OF THE INVENTION

In one aspect, the present invention is directed to an apparatus for manipulating a dental device comprising first and second gripping elements rotatably coupled to one another for movement between a gripping configuration in which a first gripping surface of the first gripping element is positioned adjacent a second gripping surface of the second gripping element to grip a dental device there between and a release configuration in which the first and second gripping surfaces are spaced from one another and wherein each of the first and second gripping surfaces includes a device receiving recess shaped to accommodate a gripping portion of a device to be gripped by the apparatus. In addition, the apparatus includes a locking mechanism for locking the first and second gripping elements in the gripping configuration.

In another aspect, the invention is directed to a carrier for a dental device, comprising a grasping portion adapted to releasably retain a gripping head of the dental device and to control angular movement of a body of the dental device, shaped surfaces of the grasping portion complementing a shape of the gripping head, a seating portion adapted to apply a seating force to a bearing surface of the dental device, and a handle to manipulate the carrier.

In yet another aspect, the invention is directed to a method of placing a dental device in a tooth. The method includes retaining a gripping head of the dental device in a gripping portion of a carrier, the gripping portion conforming to a shape of the gripping head, rotating a body of the dental device to a desired angular orientation, locking the gripping portion to prevent loss of the dental device, and manipulating the carrier to place the dental device in a desired location in the tooth.

DETAILED DESCRIPTION

Figure 1:
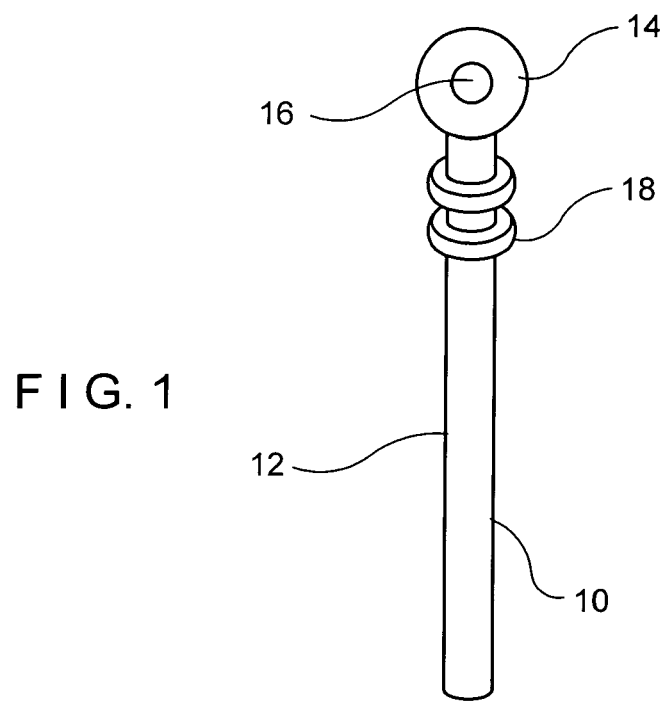
FIG. 1 is a side elevation view of a conventional post carrier, with an enlarged side elevation view of a prefabricated post.

The present invention may be further understood with reference to the following description and the appended drawings, wherein like elements are referred to with the same reference numerals. According to embodiments of the present invention, a method and device is provided to safely transport and position posts, screws, pins and other dental devices into a patient's teeth, and positively seat those dental devices in the patient's teeth. The restoration of vital and non-vital teeth are examples of procedures to which the invention is applicable.

The pins, posts and screws described herein are generally referred to as dental devices, and may include small objects that are used in dental procedures. Some of these dental devices may be used to strengthen the tooth by providing anchorage or retention of the restorative materials used to build up the clinical crown to form and function. During such procedures, the need to strengthen and restore a tooth to normal function is a primary goal of the dental practitioner. As described above, the placement of small posts and other dental devices into the remaining sound tooth structure is a difficult and taxing procedure which may be dangerous to patients if these small devices are not handled properly.

The following description of methods and devices according to embodiments of the present invention focuses on the installation of a post in a tooth following root canal therapy (endontia). It will be apparent to those skilled in the art that the present invention is not limited to this procedure, and that the foregoing discussion is exemplary in nature.

Figure 2:
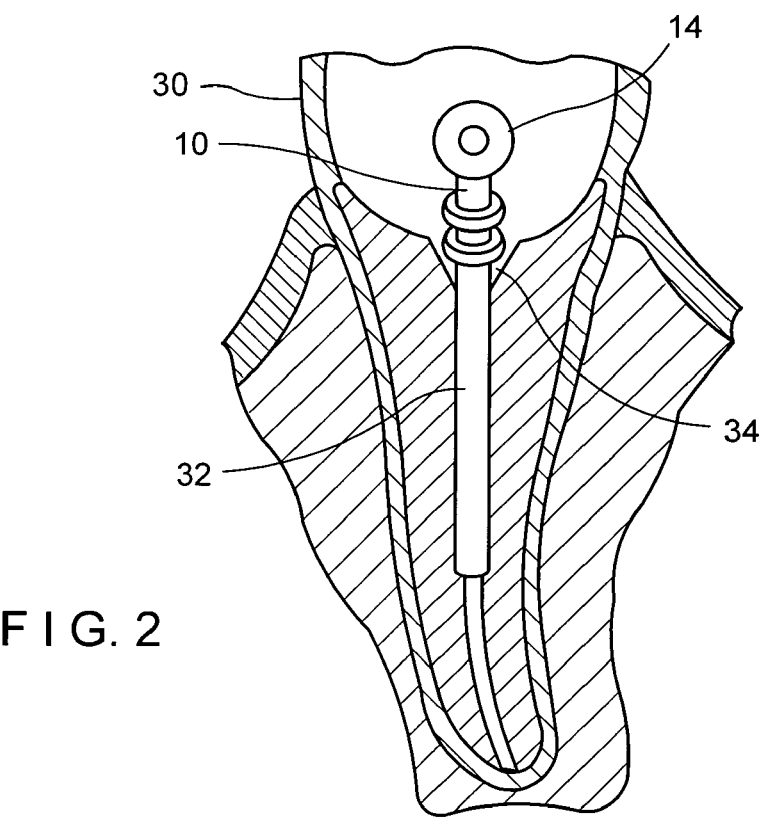
FIG. 2 is an exploded perspective view of a prefabricated post seated in the root canal of a tooth.

The exemplary post 10 has a generally elongated shape, and is made of a strong, non allergenic material such as a titanium alloy. A strong metal alloy is necessary due to the large forces that are applied to the post during mastication. Post 10 includes a body 12 and a gripping head 14 which is used to hold post 10 in the carrier at a desired angle to to enter the root canal of the tooth being treated. Body 12 fits in the root canal of the tooth as shown in FIG. 2. Those skilled in the art will understand that, although the carrier 40 is described in conjunction with a post 10 having a gripping head 14, the carrier 40 is equally effective for pins, posts and screws with no head or which are gripped by their substantially cylindrical stems.

According to exemplary embodiments of the present invention, a dental device carrier and manipulator is used in dental restorative procedures to positively control the orientation of the dental device, such as post 10, as it is inserted in the tooth. The carrier is also used to safely transport the dental device to the tooth with a reduced risk of dropping it in the mouth, and of possible ingestion by the patient. FIG.

3 shows one embodiment of the carrier 40, shown in the open configuration (a) and in the locked configuration (b), with a dental device which in this case is a post 10. The exemplary carrier 40 operates in a scissor-like manner, such that grasping portion 42 can retain post 10 when in the locked configuration, and can release it when in the open configuration. A handle 44 is provided for the user to control the opening and closing of the grasping portion 42. A locking mechanism 46 may be provided to lock the carrier 40 in the locked configuration. For example, locking mechanism 46 may be a ratchet mechanism with multiple locking positions, or may be any other appropriate locking mechanism known in the art.

Figure 4:
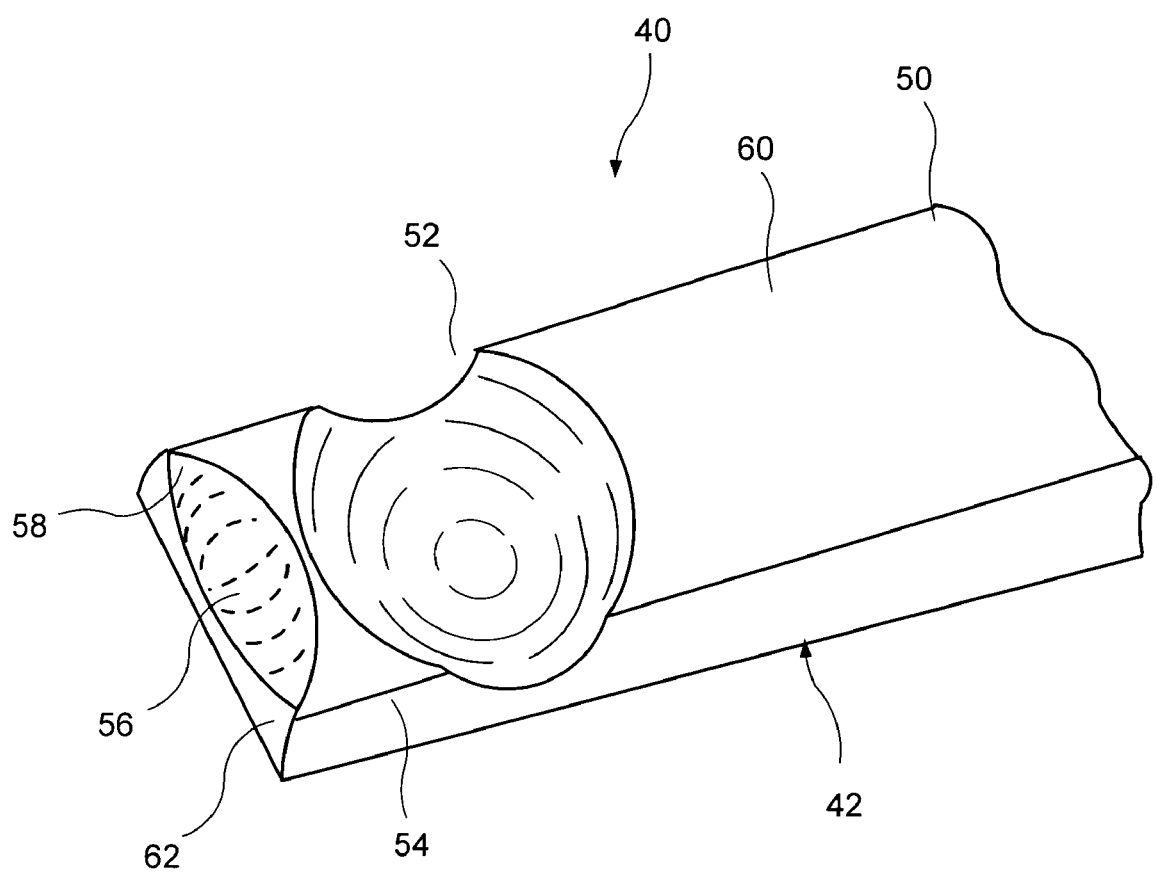
FIG. 4 is an enlarged perspective detail view of the gripping section of an arm of the dental device carrier shown in FIG. 3.

An exemplary grasping portion 42 of the carrier 40 is shown in greater detail in FIG. 4. Grasping portion 42 comprises two opposing gripping elements 50 that move relative to one another so that a distance between first operative surfaces 60 varies. In the preferred embodiment, the gripping elements 50 are formed as a pair of jaws pivotally connected so that, as they are rotated relative to one another, ends of the jaws move toward and away from one another. In this embodiment, the distance varies in response to the operation of handle 44 by the dentist. First operative surfaces 60 are each formed facing each other on one side of each gripping element 50, and are shaped so that they can act in unison to retain the gripping head 14 of post 10. When carrier 40 is in the open configuration, first operative surfaces 60 are separated by a distance greater than a dimension of gripping head 14, and do not retain it. As the distance is reduced by closing carrier 40 towards the locked configuration, first operative surfaces 60 close in on gripping head 14, and retain it there between. In this embodiment, body 12 of post 10 extends beyond grasping portion 42 at a selected angle, so that it may be inserted within tooth 30 as shown in FIG. 2.

In the exemplary embodiment, first operative surfaces 60 are shaped to conform to the shape of gripping head 14 of post 10. In this case, an indentation 52 is formed on each of first operative surfaces 60 with each of the indentations 52 being formed substantially as a portion of a sphere so that, when they are placed adjacent to one another, they substantially match that of the gripping head 14. A ball joint and socket-like connection is thus temporarily formed between carrier 40 and post 10. When a small force is used to bring together gripping elements 50, the body 12 may be moved angularly about gripping head 14 with relative ease. If the force is increased, the joint tightens so that gripping head 14 is retained in place and rotation within the spherical cavity is resisted, so that post 10 remains in the selected angular orientation until the dentist applies a force to the device. That is, when the carrier 40 is locked onto the gripping head 14, the post 10 is substantially frictionally prevented from rotating under its own weight. However, the ball and socket nature of this coupling preferably allows the dentist to rotate the gripping head 14 to any desired orientation by applying a force to the body 12 of the post 10.

In one embodiment, a stepped portion 54 may be included towards tip 58 of each of the gripping elements 50. Stepped portion 54 forms a gap between gripping elements 50 when they are brought together in the locked configuration. The gap has a dimension approximating the dimension of body 12, so that post 10 can be moved angularly across stepped portion 54 while being retained within carrier 40. The extent and shape of stepped portion 54 may be selected to limit angular movement of body 12 as desired. It will be apparent to those of skill in the art that other shapes of first operative surface 60 may be selected, without departing from the scope of the invention. Depending on the shape of gripping head 14, indentation 52 may not be hemispherical, but instead may be elliptical, parabolic, faceted, etc.

Carrier 40 also includes a seating portion, which in this example includes a second operative surface 62 formed facing forward at the tip 58 of grasping portion 42. The second operative surface 62 may be used, for example, to seat any post 10 which has previously been seated in a tooth 30 and may be particularly useful to seat a post 10 which has a shank which must seat on the face of the tooth 30. As described above in regard to the indentations 52, for handling a post 10 including a substantially spherical gripping head 14, the second operative surface 62 may preferably be formed substantially as a portion of a sphere to receive a top of the gripping head 14 so that pressure applied to the carrier 40 will be transmitted via the surface 62 to the post 10 to seat it. In this example, second operative surface 62 is divided in two halves (each forming a separate seating surface), each being formed at the tip 58 of a corresponding one of the gripping elements 50. The second operative surface 62 thus includes two indentations 56, one on each of gripping elements 50, which when brought together cooperate to form a substantially hemispherical concave surface or a concave surface which forms less than half a sphere. It will be apparent to those of skill in the art that the second operative surface 62 does not have to be formed by two parts, and does not have to be located at the tip 58 of gripping elements 50. The second operative surface 62 may be used, for example, to apply a force to the post 10 to maintain the post 10 in a fully seated position until the luting material has fully set.

Any location on carrier 40 may be used, as long as the dentist using the device may apply the second operative surface 62 to the gripping head 14 to apply a seating force to the post 10. It will also be apparent that additional shapes other than a partially indentations 56 may be used depending on the shape of the bearing surface formed on the post 10.

Figure 3A:
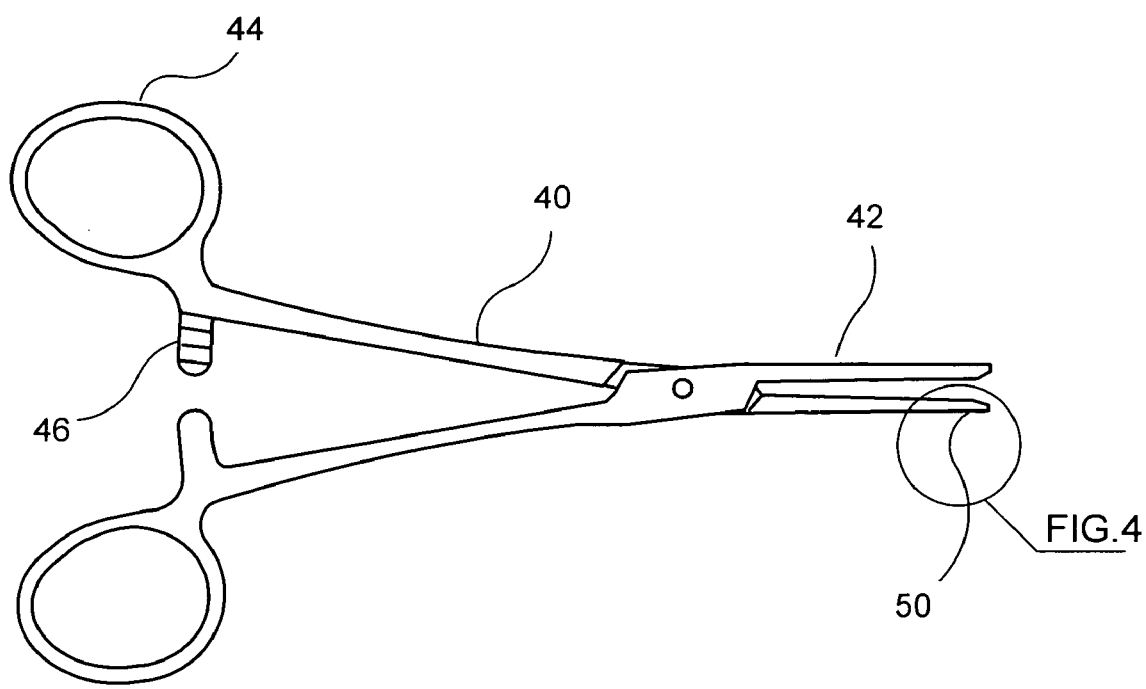
FIG. 3a is a side elevation view of the dental device carrier according to an embodiment of the present invention shown in the open configuration.
Figure 3B:
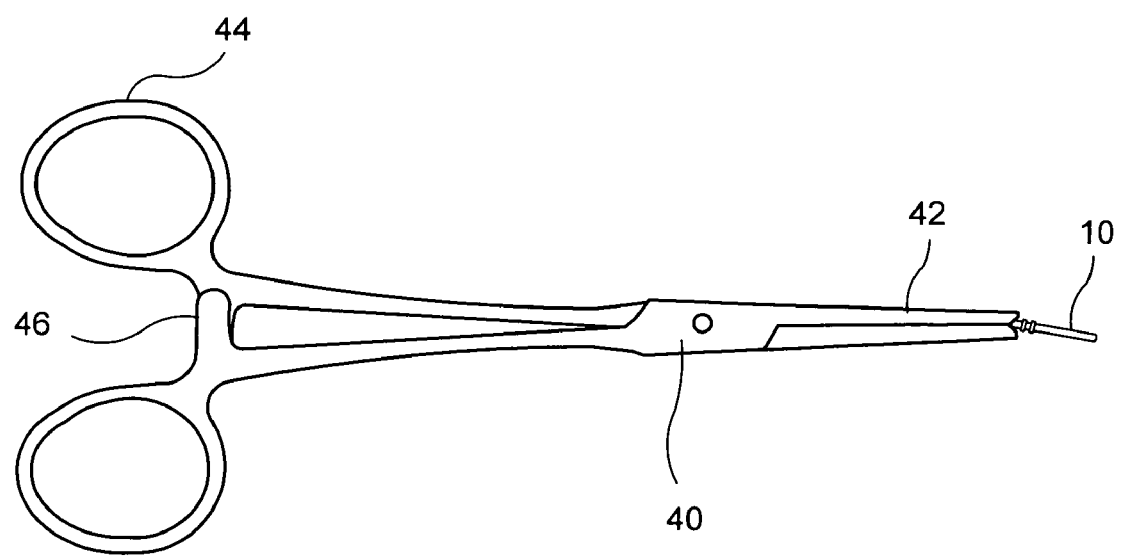
FIG. 3b is a side elevation view of the dental device of FIG. 3a in the locked configuration with a prefabricated post gripped thereby.

A procedure for utilizing the system according to the present invention in restoring an endontically treated tooth is described with reference to FIGS. 2, 3 and 4. The post carrier 40 is used to transport the post 10 to the tooth 30 and to facilitate its insertion into the post hole during try-in. Proper and rapid seating of the post 10 can thus be ensured by using the post carrier 40. The gripping head 14 of the post 10 is manually placed between the gripping elements 50 of the carrier 40, so that the spherical gripping head 14 is retained in the cavity formed by the indentations 52. After body 12 has been maneuvered to a desired angular direction, the carrier 40 is tightened to the locked configuration to prevent further movement of the post 10 relative to the carrier 40. The post 10 may then be safely transported to the tooth 30 being treated, and can be manipulated to insert it into a post hole formed in the root canal 32. Since the carrier 40 is maintains a positive lock on the post 10, the dentist is able to orient the body 12 to easily enter the post hole formed in the root canal 32 at the desired angle simply by manipulating the prefabricated post 10 held in the closed haws of the carrier 40 and the overall safety of the operation is enhanced.

After the post 10 has been inserted in the tooth 30, the carrier 40 is unlocked and moved to the open configuration, to release gripping head 14. Second operative surface 62 is then used to press down on gripping head 14, to ensure post 10 is properly seated in root canal 32. This step promotes a strong bond and correct positioning of post 10 within the tooth 30.

FIG. 2 and the foregoing discussion refer in particular to restoration of anterior and bicuspid teeth. When it is necessary to restore molar teeth, especially non-vital molar teeth, the preferred technique is to place more than one post in each tooth, to increase the coronal strength of the core material used in the restoration. Molar teeth have multiple root canals, and to maximize the strength of the restoration the posts should not be placed parallel to one another. For upper molars, the upper molar palatal root is generally the principal root canal in which the post is placed. A second post that is narrower and shorter may be placed in the mesio-buccal or disto-buccal root canals. For lower molars, the principal post is generally placed in the molar distal canal, while smaller supplementary posts are placed in a second mesio-buccal or mesio-lingual canal. The preparation of the root canal to receive the post is generally conventional, as described above.

Those skilled in the art will understand that, when placing multiple posts 10 in a multi-rooted tooth, it may be beneficial to utilize more than one carrier 40 to facilitate pick-up and placement of the posts 10 in an efficient manner. This allows the dentist to seat the posts 10 prior to set of the cementing medium used in the procedure.

The present invention has been described with reference to specific embodiments associated with the insertion of dental posts in teeth during restorative procedures. However, other embodiments may be devised that are applicable to other dental devices and procedures, without departing from the scope of the invention. Accordingly, various modifications and changes may be made to the described embodiments without departing from the broadest spirit and scope of the present invention as set forth in the claims that follow. The specification and drawings are accordingly to be regarded in an illustrative rather than restrictive sense.

What is claimed is:

1. Apparatus for manipulating a dental device comprising:
   first and second gripping elements rotatably coupled to one another for movement between a gripping configuration in which a first gripping surface of the first gripping element is positioned adjacent a second gripping surface of the second gripping element to grip a dental device there between and a release configuration in which the first and second gripping surfaces are spaced from one another and wherein each of the first and second gripping surfaces includes a device receiving recess forming a portion of a sphere to accommodate a substantially spherical gripping portion of a device to be gripped by the apparatus;
   a first seating surface on the first gripping element and a second seating on the second gripping element wherein, when the first and second gripping elements are in the gripping configuration, the first and second seating surfaces are adjacent one another to form a seating recess shaped to accommodate a gripping portion of a device to be gripped by the apparatus, wherein the first and second seating surfaces are formed in portions of the first and second gripping elements substantially perpendicular to portions thereof in which the first and second gripping surfaces are formed; and
   a locking mechanism for locking the first and second gripping elements in the gripping configuration.

2. The apparatus according to claim 1, further comprising a first handle portion extending from the first gripping element and a second handle portion extending from the second gripping element so that movement of the first and second handle portions toward one another rotates the first and second gripping elements into the gripping configuration.

3. The apparatus according to claim 1, wherein the seating recess forms a part of a sphere.

4. The apparatus according to claim 1, wherein the device receiving recesses of the first and second gripping surfaces are substantially hemispherical.

5. The apparatus according to claim 1, further comprising a stepped portion of the first and second gripping surfaces to provide clearance for a body to the dental device when the first and second gripping elements are in the gripping configuration.

6. The apparatus according to claim 1, wherein the first and second seating surfaces are formed at tips of the first and second gripping elements, respectively.

7. The instrument according to claim 1, wherein the device receiving recesses are sized and shaped to accommodate one of a post, a screw and a pin.

8. A carrier for a dental device comprising:
   first and second gripping elements rotatably coupled to one another and adapted to releasably retain a portion of a dental device and to control angular movement of a body of the dental device relative to the first and second gripping elements;
   substantially spherical surfaces of the first and second gripping elements complementing a spherical shape of the portion of the device to be gripped;
   seating surfaces formed on the first and second gripping elements, the seating surfaces cooperating with one another when the first and second gripping elements are adjacent to one another to form a seating recess for the application of a seating force to a bearing surface of the dental device, wherein the seating surfaces are formed distally of the substantially spherical surfaces of the first and second gripping elements; and
   a handle to manipulate the first and second gripping elements.

9. The carrier according to claim 8, wherein the first and second gripping elements retain the portion of the device to be grasped by friction.

10. The carrier according to claim 8, wherein the shaped surfaces are two opposing shaped surfaces.

11. The carrier according to claim 8, wherein the handle controls a distance between the shaped surfaces.

12. The carrier according to claim 8, further comprising a locking mechanism to retain a selected distance between the shaped surfaces.

13. The carrier according to claim 8, wherein each of the seating surfaces is a concave bearing surface forming part of a sphere.

14. The carrier according to claim 8, wherein the first and second gripping elements are pivotally joined at a fulcrum.

15. The carrier according to claim 8, wherein the portion of the device to be gripped is a partially spherical gripping head and wherein the first and second gripping elements, when in a gripping configuration, are adapted to form a socket for a ball portion of the gripping head, forming a ball and a socket joint.

16. The carrier according to claim 8, wherein the seating portion is aligned so that a seating force applied thereby is substantially co-axial with the body of the dental device.

17. The carrier according to claim 8, wherein when the dental device is retained by the grasping portion, the body of the dental device is perpendicular to the handle.

18. A method of placing a dental device on a tooth comprising the steps of:
   rotating first and second gripping elements of a carrier into a gripping configuration to retain a portion oft dental device in a gripping portion of the first and second gripping elements by forming a ball and socket joint connection between a substantially spherical portion of the device and a pair of opposing concave surfaces of the gripping portion, forming a portion of a sphere.

rotating a body of the dental device relative to the first and second gripping elements to a desired angular orientation;

locking the gripping portion to prevent loss of the dental device; and manipulating the carrier to place the dental device in a desired location relative to the tooth.

19. The method according to claim 18, further comprising the step of seating the dental device in the tooth by applying a seat force to a bearing surface of the dental device via a seating surface formed, when the first and second gripping elements are adjacent to one another by complementary surfaces formed at the ends thereof.

* * * * *